US008802585B2

(12) United States Patent
Weiner et al.

(10) Patent No.: US 8,802,585 B2
(45) Date of Patent: *Aug. 12, 2014

(54) CATALYSTS FOR PRODUCING ACRYLIC ACIDS AND ACRYLATES

(75) Inventors: Heiko Weiner, Pasadena, TX (US); Josefina T. Chapman, Houston, TX (US); Alexandra S. Locke, Salt Lake City, UT (US); Craig T. Peterson, Houston, TX (US); Mark O. Scates, Houston, TX (US); Dick Nagaki, The Woodlands, TX (US)

(73) Assignee: Celanese International Corporation, Dallas, TX (US)

( * ) Notice: Subject to any disclaimer, the term of this patent is extended or adjusted under 35 U.S.C. 154(b) by 206 days.

This patent is subject to a terminal disclaimer.

(21) Appl. No.: 13/240,357

(22) Filed: Sep. 22, 2011

(65) Prior Publication Data

US 2013/0079553 A1 Mar. 28, 2013

(51) Int. Cl.
| | |
|---|---|
| B01J 23/00 | (2006.01) |
| B01J 27/00 | (2006.01) |
| B01J 27/198 | (2006.01) |
| B01J 31/00 | (2006.01) |
| C07B 35/00 | (2006.01) |
| C07C 51/00 | (2006.01) |
| C07C 51/42 | (2006.01) |

(52) U.S. Cl.
USPC ........... 502/150; 502/158; 502/172; 502/208; 502/209; 502/350; 502/353; 562/599; 562/600

(58) Field of Classification Search
CPC .. B01J 21/063; B01J 35/1028; B01J 35/1023; B01J 35/1019; B01J 35/1014; B01J 27/198; B01J 27/14; B01J 23/32; B01J 21/16; B01J 37/00; B01J 35/1061; B01J 35/1057; B01J 35/1052; C07B 35/00; C07C 51/00
USPC ......... 502/150, 172, 158, 208, 209, 350, 353; 562/599, 600
See application file for complete search history.

(56) References Cited

U.S. PATENT DOCUMENTS

| | | | |
|---|---|---|---|
| 3,464,930 A * | 9/1969 | Goehre et al. | 502/309 |
| 3,799,886 A | 3/1974 | Felice et al. | |
| 4,448,897 A | 5/1984 | Gastinger | |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,364,824 A | 11/1994 | Andrews et al. | |
| RE35,377 E | 11/1996 | Steinberg et al. | |
| 5,599,976 A | 2/1997 | Scates et al. | |
| 5,821,111 A | 10/1998 | Gaddy et al. | |
| 6,143,930 A | 11/2000 | Singh et al. | |
| 6,232,352 B1 | 5/2001 | Vidalin | |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 7,005,541 B2 | 2/2006 | Cheung et al. | |
| 7,115,772 B2 | 10/2006 | Picard et al. | |
| 7,208,624 B2 | 4/2007 | Scates et al. | |
| 7,569,508 B2 * | 8/2009 | Zhou et al. | 502/150 |
| 8,501,652 B2 * | 8/2013 | Johnston et al. | 502/100 |
| 8,507,721 B2 * | 8/2013 | Herzog et al. | 562/599 |
| 2010/0197959 A1 * | 8/2010 | Johnston et al. | 560/265 |
| 2012/0071688 A1 | 3/2012 | Herzog et al. | |
| 2012/0277466 A1 * | 11/2012 | Nagaki et al. | 562/599 |
| 2012/0289743 A1 * | 11/2012 | Nagaki et al. | 562/599 |
| 2013/0053599 A1 * | 2/2013 | Weiner et al. | 560/211 |
| 2013/0085293 A1 * | 4/2013 | Nagaki et al. | 562/599 |
| 2013/0245311 A1 * | 9/2013 | Nagaki et al. | 560/211 |
| 2013/0317254 A1 * | 11/2013 | Kotsianis et al. | 562/599 |

FOREIGN PATENT DOCUMENTS

| | | | |
|---|---|---|---|
| EP | 0 643 991 A1 | 3/1995 | |
| WO | 2012/148837 | * 11/2012 | B01J 23/22 |
| WO | 2013/043385 | * 3/2013 | B01J 23/22 |

OTHER PUBLICATIONS

William E. Slinkard et al., "Vanadium-Titanium Oxide Catalysts for Oxidation of Butene to Acetic Acid", Journal of Catalysis, 68, 423-432 (1981).
International Search Report and Written Opinion mailed Apr. 25, 2013 in corresponding International Application No. PCT/US2012/054075.
M. Ai, Journal of Catalyst, 107, pp. 201-208 (1987).
M. Ai, Journal of Catalyst, 124, pp. 293-296 (1990).
M. Ai., Applied Catalysis, 36, pp. 221-230 (1988).
M. Ai., Shokubai, 29, 522, (1987), which can be found at www.shokubai.org/jnl/cgi-bin/ccotw.cgi.
Bosman, et al., J. Catalysis, vol. 148, (1994), p. 660.
Monros, et al., J. Materials Science, vol. 28, (1993), p. 5832.
Jubb & Bowen, J. Material Science, vol. 22, (1987), pp. 1963-1970.
Iler R.K., The Chemistry of Silica, (Wiley, New York, 1979).
Brinker C J & Scherer G W, Sol-Gel Science, Academic Press (1990).
M. Ai, Journal of Catalyst, 113, pp. 562-566 (1988).
M. Ai, Applied Catalysis, 48, pp. 51-61 (1989).

* cited by examiner

*Primary Examiner* — Patricia L Hailey

(57) ABSTRACT

In one embodiment, the invention is to a catalyst composition comprising vanadium and titanium. The catalyst composition has a surface area of at least 22.6 m²/g and a plurality of pores, and the plurality of pores have a pore diameter of less than 11.9 nm.

39 Claims, No Drawings

CATALYSTS FOR PRODUCING ACRYLIC ACIDS AND ACRYLATES

FIELD OF THE INVENTION

The present invention relates generally to the production of acrylic acid. More specifically, the present invention relates to catalysts used in the production of acrylic acid via the condensation of acetic acid and formaldehyde.

BACKGROUND OF THE INVENTION

α,β-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process utilizes the reaction of acetylene with water and carbon monoxide or the reaction of an alcohol and carbon monoxide to yield the acrylate ester. Another conventional process involves the reaction of ketene (often obtained by the pyrolysis of acetone or acetic acid) with formaldehyde. These processes have become obsolete for economic, environmental, or other reasons.

Another acrylic acid production method utilizes the condensation of formaldehyde and acetic acid and/or carboxylic acid esters. This reaction is often conducted over a catalyst. For example, condensation catalysts consisting of mixed oxides of vanadium and phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, Shokubai, 29, 522 (1987). The acetic acid conversions in these reactions, however, may leave room for improvement.

Thus, the need exists for improved processes for producing acrylic acid, and for improved catalysts capable of providing high acetic acid conversions in the formation of acrylic acid.

SUMMARY OF THE INVENTION

In one embodiment, the invention is to a catalyst composition comprising vanadium and titanium. Preferably, the catalyst composition has a surface area of at least 22.6 m$^2$/g, e.g., at least 30 m$^2$/g or at least 38 m$^2$/g. In one embodiment, the catalyst composition comprises a plurality of pores and the plurality of pores, collectively, has a pore diameter of less than 11.9 nm, e.g., less than 10.5 nm or less than 9 nm. In some embodiments, the inventive catalyst further comprises a dispersing agent.

In another embodiment, the present invention is to a process for producing the above-mentioned catalyst composition. The process comprises the step of contacting a titanium precursor, a vanadium precursor, phosphoric acid, and a dispersing agent selected from the group consisting of a polyacrylic acid, a polyvinyl alcohol, a polysiloxane, an ionic surfactant and a clay, to form a catalyst precursor mixture. The process further comprises the step of drying the catalyst precursor mixture to form the catalyst composition.

In another embodiment, the present invention is to a process for producing acrylic acid. The process comprises the step of contacting acetic acid and an alkylenating agent over the inventive catalyst under conditions effective to produce acrylic acid and/or acrylate.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. One process for producing these acids and esters involves the aldol condensation of formaldehyde and (i) acetic acid and/or (ii) ethyl acetate over a catalyst. Exemplary classes of conventional catalysts for this reaction include binary vanadium-titanium phosphates, vanadium-silica-phosphates, and alkali metal-promoted silicas, e.g., cesium- or potassium-promoted silicas. The alkali metal-promoted silicas, however, have been known to exhibit only low to moderate activity when used in aldol condensation reactions. As a result, the alkali metal-promoted silicas typically require metal dopants, e.g., bismuth, lanthanum, lead, thallium, and tungsten, to improve catalyst performance.

Binary vanadium-titanium phosphates have been studied with regard to the condensation of acetic acid and formaldehyde (or a methanol/oxygen mixture) to form acrylic acid. Catalysts with a vanadium:titanium:phosphorus molar ratio of 1:2:x, where x is varied from 4.0 to 7.0, have traditionally shown that the catalyst activity decreases steadily as the phosphorus content increased (see, for example M. Ai, *J. Catal.*, 107, 201 (1987); M. Ai, *J. Catal.*, 124, 293 (1990); M. Ai, *Appl. Catal.*, 36, 221 (1988); and M. Ai, Shokubai, 29, 522 (1987), discussed above). Although these catalysts may yield some aldol condensation products, e.g., acrylic acid and methyl acrylate, the conversions and selectivities are lower than desired.

Vanadyl pyrophosphate ((VO)$_2$P$_2$O$_7$) catalysts have also been extensively studied. In particular, vanadyl pyrophosphates in combination with other phosphates, i.e., titanium pyrophosphate (TiP$_2$O$_7$), have been investigated and have shown significant catalytic activity in the condensation of carboxylic acids and esters with formaldehyde. Several studies have shown that vanadium-titanium-phosphorus ternary oxides may demonstrate good catalytic performance in the aldol condensation of acetic acid with methanol/formaldehyde. In comparison, TiO$_2$, V$_2$O$_5$—TiO$_2$, and TiO$_2$—P$_2$O$_5$ were not found to be as effective. The best performance of these combinations of (VO)$_2$P$_2$O$_7$ and TiP$_2$O$_7$, however, has been obtained with a (VO)$_2$P$_2$O$_7$:TiP$_2$O$_7$ molar ratio of 1:4. At the (VO)$_2$P$_2$O$_7$:TiP$_2$O$_7$ molar ratio of 1:4, the molar ratio of vanadium:titanium:phosphorus in the resulting composition is 1:2:5. Thus, the (VO)$_2$P$_2$O$_7$/TiP$_2$O$_7$ catalyst systems that provided the highest yields (under the respective reaction conditions) were those having a vanadium to titanium ratio of about 0.5:1. Further, these studies have not investigated the use of the particular dispersing agents that are employed in the present invention.

Catalyst Composition

In one embodiment, the present invention is to a catalyst composition comprising vanadium and titanium. It has now been discovered that the addition of some dispersing agents, e.g., organic polymeric additives, to the catalyst precursor(s) during the preparation of the inventive catalyst composition surprisingly and unexpectedly provides a catalyst composition that, when used in an aldol condensation of alkylenating agent and an alkanoic acid form acrylic acid and/or other acrylate products, shows an increase in alkanoic acid conversion without showing a decrease in alkanoic acid selectivity. Without being bound by theory, it is believed that the use of these dispersing agents may inter alia 1) increase in the overall surface area of the catalyst composition; 2) improve dispersion of V and Ti throughout the catalyst composition; and/or 3) increase the $V^{4+}/V^{5+}$ ratio in the catalyst composition. In one preferred embodiment, the dispersing agent is selected from the group consisting of polymers having such functional groups such as polyacrylic acid, polyvinyl alcohols, poly(methyl methacrylate), poly(ethylene oxide), poly(ethylene glycol), polyethylenimine, copolymers, ionic surfactants, polysiloxanes, or block copolymers.

In some embodiments, the active phase of the catalyst may comprise a detectable amount of dispersing agents along with the titanium and the vanadium. As such, in some embodiments, the resultant catalyst composition may comprise from 0.01 wt. % to 10 wt. % dispersing agent, e.g., from 0.1 wt. % to 5 wt. % or from 1 wt. % to 3 wt. %. In terms of lower limits, the resultant catalyst composition may comprise at least 0.01 wt. % of the agent, e.g., at least 0.1 wt. % or at least 1.0 wt. %. Preferably, these limits and ranges apply to an active phase of the catalyst composition. The active phase is the portion of the catalyst composition comprising the components that promote the catalysis.

In other embodiments, the dispersing agent is disintegrated, evaporated from the resultant catalyst composition, and/or burned off of the resultant catalyst composition, e.g., in the drying or calcination step. As a result, little or no dispersing agent remains in the resultant catalyst composition.

Regardless of whether an amount of the dispersing agent remains in the resultant catalyst composition, the inventive catalyst composition has a higher surface area than a similar catalyst composition formed from similar starting materials, but without employing the dispersing agent(s), e.g., at least 30% higher, 40% higher, 50% higher or at least 60% higher. For example, in one embodiment, the catalyst composition has a surface area of greater than 22.6 $m^2/g$, e.g., at least 30 $m^2/g$ or at least 38 $m^2/g$, as determined by BET measurements. In terms of ranges, the surface area may range from 22.6 $m^2/g$ to 100 $m^2/g$, e.g., from 30 $m^2/g$ to 80 $m^2/g$ or from 38 $m^2/g$ to 60 $m^2/g$, as determined by BET measurements. In some embodiments, the catalyst composition has pores and the pores, collectively, have an average pore diameter ranging from 1.0 nm to 11.9 nm, e.g., from 5.0 nm to 11.9 nm, from 5.0 nm to 10.5 nm, from 7.0 nm to 10.5 nm or from 8.0 nm to 9.0 nm. In terms of limits, the pores of the catalyst composition may have an average pore diameter of less than 11.9 nm, e.g., less than 10.5 nm or less than 9 nm. Such an average pore diameter is significantly less than that of a similar catalyst composition formed from similar materials, but without employing the dispersing agent(s).

It has now been found that the inventive catalyst compositions comprising vanadium and titanium, and optionally the dispersing agent, that are prepared with the dispersing agent surprisingly and unexpectedly achieve high alkanoic acid, e.g., acetic acid, conversions when utilized in, for example, aldol condensation reactions of alkanoic acid(s) and alkylenating agents. For example, depending on the temperature at which the alkanoic acid formation reaction is conducted, alkanoic acid conversions of at least 20 mol. %, e.g., at least 30 mol. %, e.g., at least 40 mol. %, or at least 50 mol. %, may be achieved with the inventive catalyst compositions. This increase in alkanoic acid conversion is achieved while maintaining selectivity to the desired acrylates, e.g., acrylic acid and/or methyl acrylate. For example, selectivities to the desired acrylate (optionally acrylic acid and/or methyl acrylate) of at least 50 mol. %, e.g., at least 60 mol. %, at least 65 mol. %, or at least 70 mol. %, may be achieved with the catalyst of the present invention. As a result, acrylate space time yield is improved, e.g., by at least 30%, at least 40% or at least 50% over comparable catalysts having the same components in the active phase, but formed without the use of dispersing agents.

The total amounts of vanadium and titanium in the catalyst compositions, e.g., in the active phase of the catalyst compositions, of the invention may vary widely. In some embodiments, for example, the catalyst comprises at least 1 wt. % vanadium, e.g., at least 8 wt. % or at least 13 wt. %, based on the total weight of the catalyst. The catalyst composition may comprise at least 5 wt. % titanium, e.g., at least 10 wt. % or at least 12 wt. %. In terms of ranges, the catalyst composition may comprise from 1 wt. % to 40 wt. % vanadium, e.g., from 1 wt. % to 30 wt. %, from 8 wt. % to 17 wt. % or from 13 wt. % to 16 wt. % vanadium; and from 5 wt. % to 40 wt. % titanium, e.g., from 5 wt. % to 15 wt. %, from 10 wt. % to 16 wt. % or from 10 wt. % to 13 wt. % titanium. The catalyst composition preferably comprises vanadium and titanium, in combination, in an amount greater than 20 wt. %, e.g., greater than 25 wt. % or greater than 35 wt. %. In terms of ranges, the combined weight percentage of the vanadium and titanium components may range from 6 wt. % to 80 wt. %, e.g., from 25 wt. % to 60 wt. % or from 30 wt. % to 50 wt. %. In one embodiment, the molar ratio of vanadium to titanium in the active phase of the catalyst composition may be greater than 0.5:1, e.g., greater than 0.75:1, greater than 1:1, or greater than 1.25:1. In terms of ranges, the molar ratio of vanadium to titanium in the inventive catalyst composition may range from 0.5:1 to 20:1, e.g., from 0.5:1 to 10:1, or from 1:1 to 10:1.

In other embodiments, the inventive catalyst composition may further comprise other compounds or elements (metals and/or non-metals). For example, the catalyst composition may further comprise phosphorus and/or oxygen. In these cases, the catalyst composition may comprise from 15 wt. % to 45 wt. % phosphorus, e.g., from 20 wt. % to 35 wt. % or from 23 wt. % to 27 wt. %; and/or from 30 wt. % to 75 wt. % oxygen, e.g., from 35 wt. % to 65 wt. % or from 48 wt. % to 51 wt. %.

In some embodiments, at least some of the titanium is present in compound form such as in the form of titanium dioxide. For example, the catalyst composition may comprise titanium dioxide in an amount ranging from 0.1 wt. % to 95 wt. %, e.g., from 5 wt. % to 50 wt. % or from 7 wt. % to 25 wt. %. Some of the titanium dioxide, in some cases, may be in the rutile and/or anatase form, however, this amount of rutile and/or anatase titanium dioxide advantageously may be reduced as a result of the addition of the oxide additive. Preferably less than 20 wt. % of the titanium dioxide, if present in the catalyst, is in rutile form, e.g., less than 10 wt. %, less than 5 wt. %, less than 1 wt. %, or less than 0.1 wt. %. It is contemplated, however, that the catalyst composition, in some embodiments, may comprise a minor amount of rutile titanium dioxide in an amount of at least 5 wt. %, e.g., at least 10 wt. % or at least 20 wt. %. In one embodiment, less than 20 wt. % of the titanium dioxide, if present in the catalyst composition, is in anatase form, e.g., less than 10 wt. %, less than 5 wt. %, less than 1 wt. %, or less than 0.1 wt. %. It is contemplated, however, that the catalyst composition, in some embodiments, may comprise a minor amount of anatase titanium dioxide in an amount of at least 5 wt. %, e.g., at least 10 wt. % or at least 20 wt. %.

In another embodiment, the titanium is present in the form of amorphous titanium hydroxide gel, which is preferably converted to $TiP_2O_7$. The titanium hydroxide gel may be prepared by any suitable means including, but not limited to, the hydrolysis of titanium alkoxides, substituted titanium alkoxides, or titanium halides. In other embodiments, colloidal titania sols and/or dispersions may be employed. In one embodiment, titania coated colloidal particles or supports are used as a source of titanium dioxide. The hydrous titania may be amorphous or may contain portions of anatase and/or rutile depending on preparation method and heat treatment.

Upon treatment with a phosphating agent, the various forms of titania may be converted to titanium phosphates and/or titanium pyrophosphates. In some cases, a portion of the titanium may be present as unconverted titania and, hence, will be present in the final catalyst as amorphous, anatase, and/or rutile forms.

Generally speaking, the proportion of the crystalline forms of titania present in the catalyst is dependent on the titanium precursor, the preparative method, and/or the post-phosphorylating treatment. In one embodiment, the amount of anatase and rutile present in the active phase of the catalyst is minimized. The amount of crystalline titania, however, may be high with only a thin shell of porous catalyst existing on the titania support.

In one embodiment, a pentavalent vanadium compound is reduced to form the catalyst composition. The reduced pentavalent compound may be combined with a phosphorus compound and, optionally, promoters under conditions effective to provide or maintain the vanadium in a valence state below +5 to form the active metal phosphate catalysts. In addition to the dispersing agent(s), other additives, e.g., reducing agents, and solvents may be employed in the preparation of the catalyst compositions. Examples include organic acids, alcohols, polyols, aldehydes, and hydrochloric acid (other than the above-mentioned dispersing agents).

In one embodiment, suitable vanadium compounds that serve as a source of vanadium in the catalyst contain pentavalent vanadium and include, but are not limited to, vanadium pentoxide or vanadium salts such as ammonium metavanadate, vanadium oxytrihalides, vanadium alkylcarboxylates, vanadium tetraoxide, vanadium oxysulfate, oxyvanadium carboxylate salt, vanadium oxyacetylacetonate complex, or vanadic acid and mixtures thereof.

In one embodiment, suitable phosphorus compounds that serve as a source of phosphorus in the catalyst contain pentavalent phosphorus and include, but are not limited to, phosphoric acid, ammonium phosphates, phosphorus pentoxide, polyphosphoric acid, or phosphorus perhalides such as phosphorus pentachloride, and mixtures thereof.

Preferably, the active phase of the catalyst corresponds to the formula

$$V_aTi_bP_cO_d(\text{dispersing agent})_e$$

wherein the letters a, b, c, d, and e are the relative molar amounts (relative to 1.0) of vanadium, titanium, phosphorus, oxygen, and dispersing agent, respectively, in the catalyst. In these embodiments, the ratio of e to b is preferably greater than 0.05:1, e.g., greater than 0.1:1, greater than 0.5:1, or greater than 1:1. Preferred ranges for molar variables a, b, c, d, and e are shown in Table 1. In some embodiments, the ratio of a to b is greater than 0.5:1, e.g., greater than 0.75:1, greater than 1:1, or greater than 1.25:1. In some embodiments, the active phase of the catalyst may comprise of little or no dispersing agent. Preferred ranges for molar variables a, b, c, d, and e are shown in Table 1.

TABLE 1

| | Molar Ranges | | |
|---|---|---|---|
| | Molar Range | Molar Range | Molar Range |
| A | 1 to 8 | 2 to 6 | 2 to 5 |
| B | 4 to 8 | 4 to 7 | 4 to 6 |
| C | 10 to 30 | 20 to 28 | 23 to 26 |
| D | 30 to 70 | 30 to 60 | 37 to 58 |
| E | 0 to 500 | 0 to 80 | 0 to 10 |

In another embodiment, the active phase of the catalyst corresponds to the formula:

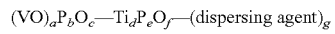
$$(VO)_aP_bO_c\text{—}Ti_dP_eO_f\text{—}(\text{dispersing agent})_g$$

wherein the letters a, b, c, d, e, f, and g are the relative molar amounts (relative to 1.0) of VO, phosphorus, and oxygen (in the $(VO)_aP_bO_c$ component); the relative molar amounts of, titanium, phosphorus, and oxygen (in the $Ti_dP_eO_f$ component); and the relative molar amount of the oxide additive(s), respectively in the catalyst. In these embodiments, the combination of b and e may range from 10 to 30, e.g., from 23 to 26, and/or the combination of a, c, and f may range from 30 to 65, e.g., from 37 to 58. In some embodiments, the active phase of the catalyst may comprise of little or no dispersing agent. Preferred ranges for molar variables a, b, c, d, e, f, and g are shown in Table 2.

TABLE 2

| | Molar Ranges | | |
|---|---|---|---|
| | Molar Range | Molar Range | Molar Range |
| a | 1 to 16 | 2 to 14 | 4 to 10 |
| b | 1 to 20 | 6 to 20 | 4 to 12 |
| c | 8 to 64 | 16 to 60 | 33 to 45 |
| d | 2 to 6 | 3 to 5 | 3 to 4 |
| e | 4 to 14 | 6 to 11 | 6 to 9 |
| f | 15 to 45 | 22 to 39 | 22 to 32 |
| g | 0 to 500 | 0 to 80 | 0 to 10 |

In some embodiments, the catalyst further comprises additional metals. These additional metals may function as promoters. If present, the additional metals may be selected from the group consisting of copper, molybdenum, tungsten, nickel, niobium, and combinations thereof. Other exemplary promoters that may be included in the catalyst of the invention include lithium, sodium, magnesium, aluminum, chromium, manganese, iron, cobalt, calcium, yttrium, ruthenium, silver, tin, barium, lanthanum, the rare earth metals, hafnium, tantalum, rhenium, thorium, bismuth, antimony, germanium, zirconium, uranium, cesium, zinc, and silicon and mixtures thereof. Other modifiers include boron, gallium, arsenic, sulfur, halides, Lewis acids such as $BF_3$, $ZnBr_2$, and $SnCl_4$. Exemplary processes for incorporating promoters into catalyst are described in U.S. Pat. No. 5,364,824, the entirety of which is incorporated herein by reference.

If the catalyst comprises additional metal(s) and/or metal oxides(s), the catalyst optionally may comprise additional metals and/or metal oxides in an amount from 0.001 wt. % to 30 wt. %, e.g., from 0.01 wt. % to 5 wt. % or from 0.1 wt. % to 5 wt. %. If present, the promoters may enable the catalyst to have a weight/weight space time yield of at least 25 grams of acrylic acid/gram catalyst-h, e.g., least 50 grams of acrylic acid/gram catalyst-h, or at least 100 grams of acrylic acid/gram catalyst-h.

In some embodiments, the catalyst is unsupported. In these cases, the catalyst may comprise a homogeneous mixture or a heterogeneous mixture as described above. In one embodiment, the homogeneous mixture is the product of an intimate mixture of vanadium and titanium oxides, hydroxides, and phosphates resulting from preparative methods such as controlled hydrolysis of metal alkoxides or metal complexes. In other embodiments, the heterogeneous mixture is the product of a physical mixture of the vanadium and titanium phosphates. These mixtures may include formulations prepared from phosphorylating a physical mixture of preformed hydrous metal oxides. In other cases, the mixture(s) may include a mixture of preformed vanadium pyrophosphate and titanium pyrophosphate powders.

In another embodiment, the catalyst is a supported catalyst comprising a catalyst support in addition to the vanadium, titanium, dispersing agent, and optionally phosphorous and oxygen, in the amounts indicated above (wherein the molar ranges indicated are without regard to the moles of catalyst support, including any vanadium, titanium, dispersing agent, phosphorous or oxygen contained in the catalyst support). The total weight of the support (or modified support), based on the total weight of the catalyst, preferably is from 75 wt. % to 99.9 wt. %, e.g., from 78 wt. % to 97 wt. % or from 80 wt. % to 95 wt. %. The support may vary widely. In one embodiment, the support material is selected from the group consisting of silica, alumina, zirconia, titania, aluminosilicates, zeolitic materials, mixed metal oxides (including but not limited to binary oxides such as $SiO_2$—$Al_2O_3$, $SiO_2$—$TiO_2$, $SiO_2$—$ZnO$, $SiO_2$—$MgO$, $SiO_2$—$ZrO_2$, $Al_2O_3$—$MgO$, $Al_2O_3$—$TiO_2$, $Al_2O_3$—$ZnO$, $TiO_2$—$MgO$, $TiO_2$—$ZrO_2$, $TiO_2$—$ZnO$, $TiO_2$—$SnO_2$) and mixtures thereof, with silica being one preferred support. In embodiments where the catalyst comprises a titania support, the titania support may comprise a major or minor amount of rutile and/or anatase titanium dioxide. Other suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, silicon carbide, sheet silicates or clay minerals such as montmorillonite, beidellite, saponite, pillared clays, other microporous and mesoporous materials, and mixtures thereof. Other supports may include, but are not limited to, iron oxide, magnesia, steatite, magnesium oxide, carbon, graphite, high surface area graphitized carbon, activated carbons, and mixtures thereof. These listings of supports are merely exemplary and are not meant to limit the scope of the present invention.

In other embodiments, in addition to the active phase and a support, the inventive catalyst may further comprise a support modifier. A modified support, in one embodiment, relates to a support that includes a support material and a support modifier, which, for example, may adjust the chemical or physical properties of the support material such as the acidity or basicity of the support material. In embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst composition.

In one embodiment, the support modifier is an acidic support modifier. In some embodiments, the catalyst support is modified with an acidic support modifier. The support modifier similarly may be an acidic modifier that has a low volatility or little volatility. The acidic modifiers may be selected from the group consisting of oxides of Group IVB metals, oxides of Group VB metals, oxides of Group VIB metals, iron oxides, aluminum oxides, and mixtures thereof. In one embodiment, the acidic modifier may be selected from the group consisting of $WO_3$, $MoO_3$, $Fe_2O_3$, $Cr_2O_3$, $V_2O_5$, $MnO_2$, $CuO$, $Co_2O_3$, $Bi_2O_3$, $TiO_2$, $ZrO_2$, $Nb_2O_5$, $Ta_2O_5$, $Al_2O_3$, $B_2O_3$, $P_2O_5$, and $Sb_2O_3$.

In another embodiment, the support modifier is a basic support modifier. The presence of chemical species such as alkali and alkaline earth metals, are normally considered basic and may conventionally be considered detrimental to catalyst performance. The presence of these species, however, surprisingly and unexpectedly, may be beneficial to the catalyst performance. In some embodiments, these species may act as catalyst promoters or a necessary part of the acidic catalyst structure such in layered or sheet silicates such as montmorillonite. Without being bound by theory, it is postulated that these cations create a strong dipole with species that create acidity.

Additional modifiers that may be included in the catalyst include, for example, boron, aluminum, magnesium, zirconium, and hafnium.

In some embodiments, the support may be a high surface area support, e.g., a support having a surface area of at least 1 $m^2/g$, e.g., at least 20 $m^2/g$ or at least 50 $m^2/g$, as determined by BET measurements. The catalyst support may include pores, optionally having an average pore diameter ranging from 5 nm to 200 nm, e.g., from 5 nm to 50 nm or from 10 nm to 25 nm. The catalyst optionally has an average pore volume of from 0.05 $cm^3/g$ to 3 $cm^3/g$, e.g., from 0.05 $cm^3/g$ to 0.1 $cm^3/g$ or from 0.08 $cm^3/g$ to 0.1 $cm^3/g$, as determined by BET measurements. Preferably, at least 50% of the pore volume or surface area, e.g., at least 70% or at least 80%, is provided by pores having the diameters discussed above. Pores may be formed and/or modified by pore modification agents, which are discussed below. In another embodiment, the ratio of microporosity to macroporosity ranges from 95:5 to 85:15, e.g., from 75:25 to 70:30. Microporosity refers to pores smaller than 2 nm in diameter, and movement in micropores may be described by activated diffusion. Mesoporosity refers to pores greater than 2 nm and less than 50 nm is diameter. Flow through mesopores may be described by Knudson diffusion. Macroporosity refers to pores greater than 50 nm in diameter and flow though macropores may be described by bulk diffusion. Thus, in some embodiments, it is desirable to balance the surface area, pore size distribution, catalyst or support particle size and shape, and rates of reaction with the rate of diffusion of the reactant and products in and out of the pores to optimize catalytic performance.

As will be appreciated by those of ordinary skill in the art, the support materials, if included in the catalyst of the present invention, preferably are selected such that the catalyst system is suitably active, selective and robust under the process conditions employed for the formation of the desired product, e.g., acrylic acid or alkyl acrylate. Also, the active metals and/or pyrophosphates that are included in the catalyst of the invention may be dispersed throughout the support, coated on the outer surface of the support (egg shell) or decorated on the surface of the support. In some embodiments, in the case of macro- and meso-porous materials, the active sites may be anchored or applied to the surfaces of the pores that are distributed throughout the particle and hence are surface sites available to the reactants but are distributed throughout the support particle.

The inventive catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

In one embodiment, the inventive catalyst composition comprises a pore modification agent. A preferred type of pore modification agent is thermally stable and has a substantial vapor pressure at a temperature below 300° C., e.g., below 250° C. In one embodiment, the pore modification agent has a vapor pressure of at least 0.1 kPa, e.g., at least 0.5 kPa, at a temperature between about 150° C. and about 250° C., e.g., between about 150° C. and about 200° C.

In some embodiments, the pore modification agent has a relatively high melting point, e.g., greater than 60° C., e.g., greater than 75° C., so that it does not melt during compression of the catalyst precursor into a slug, tablet, or pellet. Preferably, the pore modification agent comprises a relatively pure material rather than a mixture. As such, lower melting components will not liquefy under compression during formation of slugs or tablets. For example, where the pore modification agent is a fatty acid, lower melting components of the fatty acid mixtures may be removed as liquids by pressing. If this phenomenon occurs during slug or tablet compression, the flow of liquid may disturb the pore structure and produce an undesirable distribution of pore volume as a function of pore diameter on the catalyst composition. In other embodiments, the pore modification agents have a significant vapor pressure at temperatures below their melting points, so that they can be removed by sublimination into a carrier gas.

For example, the pore modification agent may be a fatty acid corresponding to the formula $CH_3(CH_2)_xCOOH$ where x>8. Exemplary fatty acids include stearic acid (x=16), palmitic acid (x=14), lauric acid (x=10), myristic acid (x=12). The esters of these acids and amides or other functionalized forms of such acids, for example, stearamide ($CH_3(CH_2)_{16}CONH_2$) may also be used. Suitable esters may include methyl esters as well as glycerides such as stearin (glycerol tristearate). Mixtures of fatty acids may be used, but substantially pure acids, particularly stearic acid, are generally preferred over mixtures.

Other preferred pore modification agents include but are not limited to polynuclear organic compounds such as naphthalene, graphite, natural burnout components such as cellulose and its cellulosic derivatives, starches, natural and synthetic oligomers and polymers such as polyvinyl alcohols and polyacrylic acids and esters.

Catalyst Preparation

In one embodiment, the inventive catalyst is formed by a process comprising the step of contacting a titanium precursor, a vanadium precursor, and a dispersing agent selected from a group consisting of a polyacrylic acid, a polyvinyl alcohol, a polysiloxane, an ionic surfactant and a clay, and optionally phosphoric acid and/or a reducing agent to form a catalyst precursor mixture. The process further comprises the step of drying, e.g., calcining the catalyst precursor mixture to form the catalyst composition. In a preferred embodiment, the contacting of the above-identified components is achieved in one or more steps, e.g. two or more steps. For example, in one embodiment, a titanium precursor, phosphoric acid, and a dispersing agent are contacted to form a titanium precursor mixture. A vanadium precursor may be contacted with a mixture of a reducing agent and a dispersing agent to form a vanadium mixture. The dispersing agent in this step may be the same as or different from the dispersing agent used in the formation of the titanium precursor mixture. Preferably, both of these steps employ the same dispersing agent. In a preferred embodiment, the titanium precursor mixture and the vanadium mixture are contacted with one another to form the catalyst precursor mixture.

In another embodiment of the present invention, the catalyst composition is formed by contacting, e.g., mixing, a titanium precursor mixture with a vanadium mixture. The titanium pyrophosphate mixture is prepared by contacting a titanium precursor with an alcohol, such as 2-propanol, ethanol, or i-butanol. The diluted titanium precursor is slowly added to a colloidal silica/dispersing agent mixture, which includes colloidal silica and a dispersing agent, optionally in water. Phosphoric acid is then slowly added to the suspension and the mixture to form the titanium pyrophosphate mixture. The vanadium mixture is separately prepared by adding a vanadium precursor to a heated dispersing agent mixture, which comprises oxalic acid dehydrate, ethylene glycol, the dispersing agent, and optionally in water. The vanadium mixture is heated and added to the titanium pyrophosphate mixture to form the inventive catalyst composition. The process further comprises the step of dying the catalyst composition and calcining the catalyst composition as described below.

In one embodiment, the drying comprises calcining at a high temperature, which yields the inventive catalyst composition. The inventive catalyst composition has a higher surface area than a corresponding catalyst composition formed without the dispersing agent.

In preferred embodiments, the titanium precursor is selected from a group consisting of $Ti(OR)_4$, $L_xTi(OR)_y$ complexes, $TiCl_z$, hydrated titania sols and colloidal $TiO_2$, wherein R=methyl, ethyl, propyl, and butyl; L=acetylacetone, or similar bidentate ligands; x=1-3; y=1-3; and z=3-4. Most preferably, the titanium precursor comprises $TiP_2O_7$ and/or $Ti(OiPr)_4$. In one preferred embodiment, the dispersing agent is polyacrylic acid. In one embodiment, the vanadium precursor comprises but not limited to ammonium metavanadate, vanadium pentoxide, vanadium tetraoxide, oxytrihalides, vanadium alkylcarboxylates, vanadium oxysulfate, oxyvanadium carboxylate salt, vanadium oxyacetylacetonate complex, or vanadic acid.

In some embodiments, e.g., embodiments where the catalyst is unsupported, the catalyst may be formed by a process comprising the step of dissolving at least one oxide additive and an acid, e.g., phosphoric acid, optionally in water, to form an additive solution comprising at least 0.04 wt. % oxide additive, e.g., at least 0.1 wt. % or at least 1 wt. %. The process may further comprise the steps of adding a titanium precursor and a vanadium precursor to the additive solution to form a catalyst precursor mixture and drying the catalyst precursor mixture to form the catalyst composition.

In preferred embodiments, where the catalyst is unsupported, the catalyst composition may be formed via a process comprising the step of dissolving at least one oxide additive and an acid, e.g., phosphoric acid, in water to form an additive solution comprising at least 0.04 wt. % oxide additive, e.g., at least 0.1 wt. % or at least 1 wt. %. The process further comprises the steps of contacting the additive solution with a titanium precursor, e.g., $TiP_2O_7$ or $Ti(OiPr)_4$, to form a titanium solution and contacting the titanium solution with a predetermined amount of a vanadium precursor, e.g., a soluble $NH_4VO_3$ solution, to form a the catalyst composition. Preferably, the process further comprises the step of drying the wet catalyst precursor to form a dried catalyst composition and optionally, further calcining the dried catalyst composition. The amounts of the titanium precursor and the vanadium precursor are determined such that the resultant dried catalyst composition has a molar ratio of vanadium to titanium greater than 0.5:1, e.g., greater than 0.75:1, greater than 1:1, or greater than 1.25:1. In one embodiment, the molar ratio of ammonium metavanadate to titanium pyrophosphate is at least 0.1:1 e.g., at least 0.5:1 or at least 1:1.

The process, in one embodiment, may further comprise calcining the dried catalyst, which, preferably, is conducted in accordance with a temperature profile. As one example, the temperature profile comprises an increasing stair step temperature profile comprising a plurality of increasing hold temperatures. The temperature increases at a rate from 1° C. to 5° C. per minute between said hold temperatures. Preferably, the hold temperatures comprise a first, second, third, and fourth hold temperature. The first hold temperature may range from 150° C. and 300° C., e.g., from 175° C. and 275° C., preferably being about 160° C. The second hold temperature may range from 250° C. and 500° C., e.g., from 300° C. and 400° C., preferably being about 250° C. The third hold temperature may range from 300° C. and 700° C., e.g., from 450° C. and 650° C., preferably being about 300° C. The fourth hold temperature may range from 400° C. and 700° C., e.g., from 450° C. and 650° C., preferably being about 450° C. Of course, other temperature profiles may be suitable. The calcination of the mixture may be done in an inert atmosphere, air or an oxygen-containing gas at the desired temperatures. Steam, a hydrocarbon or other gases or vapors may be added to the atmosphere during the calcination step or post-calcination to cause desired effects on physical and chemical surface properties as well as textural properties such as increase macroporosity.

In one preferred embodiment, the temperature profile comprises:
 i) heating the dried catalyst from room temperature to 160° C. at a rate of 10° C. per minute;
 ii) heating the dried catalyst composition at 160° C. for 2 hours;
 iii) heating the dried catalyst composition from 160° C. to 250° C. at a rate of 3° C. per minute;
 iv) heating the dried catalyst composition at 250° C. for 2 hours;
 v) heating the dried catalyst composition from 250° C. to 300° C. at a rate of 3° C. per minute;
 vi) heating the dried catalyst composition at 300° C. for 6 hours;
 vii) heating the dried catalyst composition from 300° C. to 450° C. at a rate of 3° C. per minute; and
 viii) heating the dried catalyst composition at 450° C. for 2 hours.

In another embodiment, the temperature profile comprises:
 i) contacting the catalyst composition with flowing air at a first temperature;
 ii) contacting the catalyst composition with flowing air at a second temperature greater than the first temperature; and
 iii) contacting the catalyst composition with static air at a third temperature greater than the first and second temperatures.

The first hold temperature may range from 110° C. and 210° C., e.g., from 135° C. and 185° C., preferably being about 160° C. The second hold temperature may range from 300° C. and 400° C., e.g., from 325° C. and 375° C., preferably being about 350° C. The third hold temperature may range from 400° C. and 500° C., e.g., from 425° C. and 475° C., preferably being about 450° C. In one embodiment, a first drying stage uses flowing air at 160° C. for approximately 2 hours; a second drying stage uses flowing air at 350° C. for approximately 4 hours, and a third drying stage uses static air at 450° C. for eight hours. Of course, other temperature profiles may be suitable.

In embodiments where the catalyst is supported, the catalyst compositions are formed through metal impregnation of a support (optionally modified support), although other processes such as chemical vapor deposition may also be employed.

In one embodiment, the catalysts are made by impregnating the support, with a solution of the metals or salts thereof in a suitable solvent, followed by drying and optional calcination. Solutions of the modifiers or additives may also be impregnated onto the support in a similar manner. The impregnation and drying procedure may be repeated more than once in order to achieve the desired loading of metals, modifiers, and/or other additives. In some cases, there may be competition between the modifier and the metal for active sites on the support. Accordingly, it may be desirable for the modifier to be incorporated before the metal. Multiple impregnation steps with aqueous solutions may to reduce the strength of the catalyst particles if the particles are fully dried between impregnation steps. Thus, it is preferable to allow some moisture to be retained in the catalyst between successive impregnations. In one embodiment, when using non-aqueous solutions, the modifier and/or additive are introduced first by one or more impregnations with a suitable non-aqueous solution, e.g., a solution of an alkoxide or acetate of the modifier metal in an alcohol, e.g., ethanol, followed by drying. The metal may then be incorporated by a similar procedure using a suitable solution of a metal compound.

In other embodiments, the modifier is incorporated into the composition by co-gelling or co-precipitating a compound of the modifier element with the silica, or by hydrolysis of a mixture of the modifier element halide with a silicon halide. Methods of preparing mixed oxides of silica and zirconia by sol gel processing are described by Bosman, et al., in *J Catalysis*, Vol. 148, (1994), page 660 and by Monros et al., in *J Materials Science*, Vol. 28, (1993), page 5832. Also, doping of silica spheres with boron during gelation from tetraethyl orthosilicate (TEOS) is described by Jubb and Bowen in *J Material Science*, Vol. 22, (1987), pages 1963-1970. Methods of preparing porous silicas are described in Iler R K, *The Chemistry of Silica*, (Wiley, New York, 1979), and in Brinker C J & Scherer G W *Sol-Gel Science* published by Academic Press (1990).

The catalyst composition, in some embodiments, will be used in a fixed bed reactor for forming the desired product, e.g., acrylic acid or alkyl acrylate. Thus, the catalyst is preferably formed into shaped units, e.g., spheres, granules, pellets, powders, aggregates, or extrudates, typically having maximum and minimum dimensions in the range of 1 to 25 mm, e.g., from 2 to 15 mm. Where an impregnation technique is employed, the support may be shaped prior to impregnation. Alternatively, the composition may be shaped at any suitable stage in the production of the catalyst. The catalyst also may be effective in other forms, e.g. powders or small beads and may be used in these forms. In one embodiment, the catalyst is used in a fluidized bed reactor. In this case, the catalyst may be prepared via spray drying or spray thermal decomposition. Preferably, the resultant catalyst has a particle size of greater than 300 microns, e.g., greater than 500 microns.

Production of Acrylic Acid

In other embodiments, the invention is to a process for producing unsaturated acids, e.g., acrylic acids, or esters thereof (alkyl acrylates), by contacting an alkanoic acid with an alkylenating agent, e.g., a methylenating agent, under conditions effective to produce the unsaturated acid and/or acrylate. Preferably, acetic acid is reacted with formaldehyde in the presence of the inventive catalyst composition. The alkanoic acid, or ester of an alkanoic acid, may be of the formula R'—CH$_2$—COOR, where R and R' are each, independently, hydrogen or a saturated or unsaturated alkyl or aryl group. As an example, R and R' may be a lower alkyl group containing for example 1-4 carbon atoms. In one embodiment, an alkanoic acid anhydride may be used as the source of the alkanoic acid. In one embodiment, the reaction is conducted in the presence of an alcohol, preferably the alcohol that corresponds to the desired ester, e.g., methanol. In addition to reactions used in the production of acrylic acid, the inventive catalyst, in other embodiments, may be employed to catalyze other reactions. Examples of these other reactions include, but are not limited to butane oxidation to maleic anhydride, acrolein production from formaldehyde and acetaldehyde, and methacrylic acid production from formaldehyde and propionic acid.

The acetic acid may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352, which is hereby incorporated by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syngas is diverted from the methanol synthesis loop and supplied to a separator unit to recover carbon monoxide and hydrogen, which are then used to produce acetic acid.

Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, all of which are hereby incorporated by reference.

U.S. Pat. No. RE 35,377, which is hereby incorporated by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. U.S. Pat. No. 5,821,111, which discloses a process for converting waste biomass through gasification into syngas, as well as U.S. Pat. No. 6,685,754, are hereby incorporated by reference.

In one optional embodiment, the acetic acid that is utilized in the condensation reaction comprises acetic acid and may also comprise other carboxylic acids, e.g., propionic acid, esters, and anhydrides, as well as acetaldehyde and acetone. In one embodiment, the acetic acid fed to the hydrogenation reaction comprises propionic acid. For example the propionic acid in the acetic acid feed stream may range from 0.001 wt. % to 15 wt. %, e.g., from 0.001 wt. % to 0.11 wt. %, from 0.125 wt. % to 12.5 wt. %, from 1.25 wt. % to 11.25, or from 3.75 wt. % to 8.75 wt. %. Thus, the acetic acid feed stream may be a crude acetic acid feed stream, e.g., a less-refined acetic acid feed stream.

As used herein, "alkylenating agent" means an aldehyde or precursor to an aldehyde suitable for reacting with the alkanoic acid, e.g., acetic acid, in an aldol condensation reaction to form an unsaturated acid, e.g., acrylic acid, or an alkyl acrylate. In preferred embodiments, the alkylenating agent comprises a methylenating agent such as formaldehyde, which preferably is capable of adding a methylene group (=CH$_2$) to the organic acid. Other alkylenating agents may include, for example, acetaldehyde, propanal, and butanal.

The alkylenating agent, e.g., formaldehyde, may be added from any suitable source. Exemplary sources may include, for example, aqueous formaldehyde solutions, anhydrous formaldehyde derived from a formaldehyde drying procedure, trioxane, diether of methylene glycol, and paraformaldehyde. In a preferred embodiment, the formaldehyde is produced via a formox unit, which reacts methanol and oxygen to yield the formaldehyde.

In other embodiments, the alkylenating agent is a compound that is a source of formaldehyde. Where forms of formaldehyde that are not as freely or weakly complexed are used, the formaldehyde will form in situ in the condensation reactor or in a separate reactor prior to the condensation reactor. Thus for example, trioxane may be decomposed over an inert material or in an empty tube at temperatures over 350° C. or over an acid catalyst at over 100° C. to form the formaldehyde.

In one embodiment, the alkylenating agent corresponds to Formula I.

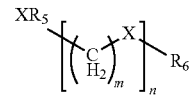

In this formula, R$_5$ and R$_6$ may be independently selected from C$_1$-C$_{12}$ hydrocarbons, preferably, C$_1$-C$_{12}$ alkyl, alkenyl or aryl, or hydrogen. Preferably, R$_5$ and R$_6$ are independently C$_1$-C$_6$ alkyl or hydrogen, with methyl and/or hydrogen being most preferred. X may be either oxygen or sulfur, preferably oxygen; and n is an integer from 1 to 10, preferably 1 to 3. In some embodiments, m is 1 or 2, preferably 1.

In one embodiment, the compound of formula I may be the product of an equilibrium reaction between formaldehyde and methanol in the presence of water. In such a case, the compound of formula I may be a suitable formaldehyde source. In one embodiment, the formaldehyde source includes any equilibrium composition. Examples of formaldehyde sources include but are not restricted to methylal (1,1 dimethoxymethane); polyoxymethylenes —(CH$_2$—O)$_i$— wherein i is from 1 to 100; formalin; and other equilibrium compositions such as a mixture of formaldehyde, methanol, and methyl propionate. In one embodiment, the source of formaldehyde is selected from the group consisting of 1,1 dimethoxymethane; higher formals of formaldehyde and methanol; and CH$_3$—O—(CH$_2$—O)$_i$—CH$_3$ where i is 2.

The alkylenating agent may be used with or without an organic or inorganic solvent.

The term "formalin," refers to a mixture of formaldehyde, methanol, and water. In one embodiment, formalin comprises from 25 wt. % to 65 wt. % formaldehyde; from 0.01 wt. % to 25 wt. % methanol; and from 25 wt. % to 70 wt. % water. In cases where a mixture of formaldehyde, methanol, and methyl propionate is used, the mixture comprises less than 10 wt. % water, e.g., less than 5 wt. % or less than 1 wt. %.

In some embodiments, the condensation reaction may achieve favorable conversion of acetic acid and favorable selectivity and productivity to acrylates. For purposes of the present invention, the term "conversion" refers to the amount of acetic acid in the feed that is converted to a compound other than acetic acid. Conversion is expressed as a mole percentage based on acetic acid in the feed. The conversion of acetic acid may be at least 11 mol. %, e.g., at least 20 mol. %, at least 40 mol. %, or at least 50 mol. %. In another embodiment, the reaction may be conducted wherein the molar ratio of acetic acid to alkylenating agent is at least 0.55:1, e.g., at least 1:1.

Selectivity is expressed as the ratio of the amount of carbon in the desired product(s) and the amount of carbon in the total products. This ratio may be multiplied by 100 to arrive at the selectivity. Preferably, the catalyst selectivity to acrylates, e.g., acrylic acid and methyl acrylate, is at least 40 mol. %, e.g., at least 50 mol. %, at least 60 mol. %, or at least 70 mol. %. In some embodiments, the selectivity to acrylic acid is at least 30 mol. %, e.g., at least 40 mol. %, or at least 50 mol. %; and/or the selectivity to methyl acrylate is at least 10 mol. %, e.g., at least 15 mol. %, or at least 20 mol. %.

The term "productivity," as used herein, refers to the grams of a specified product, e.g., acrylates, formed during the condensation based on the liters of catalyst used per hour. A productivity of at least 20 grams of acrylates per liter catalyst per hour, e.g., at least 40 grains of acrylates per liter catalyst per hour or at least 100 grams of acrylates per liter catalyst per hour, is preferred. In terms of ranges, the productivity preferably is from 20 to 500 grams of acrylates per liter catalyst per hour, e.g., from 20 to 200 grams of acrylates per kilogram catalyst per hour or from 40 to 140 grams of acrylates per kilogram catalyst per hour.

As noted above, the inventive catalyst compositions provide for high conversions of acetic acid. Advantageously, these high conversions are achieved while maintaining selectivity to the desired acrylates, e.g., acrylic acid and/or methyl acrylate. As a result, acrylate productivity is improved, as compared to conventional productivity with conventional catalysts.

The acetic acid conversion, in some embodiments, may vary depending upon the reaction temperature. In one embodiment, for example, when the reaction temperature is approximately 340° C., the acetic acid conversion is at least 11%, e.g., at least 15% or at least 25%. The selectivity to acrylates is maintained at, for example, at least 60%, e.g., at least 65%, at least 75% or at least 90%. Accordingly, the productivity, e.g., the space time yield, of acrylates is at least 29 grams per liter catalyst per hour, e.g., at least 40 grams per liter or at least 55 grams per liter, when the reaction temperature is approximately 340° C.

In another embodiment where the reaction temperature is approximately 350° C., the acetic acid conversion is at least 28%, e.g., at least 30% or at least 35%. The selectivity to acrylates is maintained at, for example, at least 60%, e.g., at least 65%, at least 75% or at least 90%. Accordingly, the productivity, e.g., the space time yield, of acrylates is at least 57 grams per liter of catalyst per hour, e.g., at least 70 grams per liter of catalyst per hour or at least 85 grams per liter of catalyst per hour, when the reaction temperature is approximately 355° C.

In another embodiment where the reaction temperature is approximately 370° C., the acetic acid conversion is at least 38%, e.g., at least 40% or at least 45%. The selectivity to acrylates is maintained at, for example, at least 60%, e.g., at least 65%, at least 75% or at least 90%. Accordingly, the productivity, e.g., the space time yield, of acrylates is at least 97 grams per liter of catalyst per hour, e.g., at least 110 grams per liter of catalyst per hour or at least 125 grams per liter of catalyst per hour, when the reaction temperature is approximately 370° C.

Preferred embodiments of the inventive process also have low selectivity to undesirable products, such as carbon monoxide and carbon dioxide. The selectivity to these undesirable products preferably is less than 29%, e.g., less than 25% or less than 15%. More preferably, these undesirable products are not detectable. Formation of alkanes, e.g., ethane, may be low, and ideally less than 2%, less than 1%, or less than 0.5% of the acetic acid passed over the catalyst is converted to alkanes, which have little value other than as fuel.

The alkanoic acid or ester thereof and alkylenating agent may be fed independently or after prior mixing to a reactor containing the catalyst. The reactor may be any suitable reactor. Preferably, the reactor is a fixed bed reactor, but other reactors such as a continuous stirred tank reactor or a fluidized bed reactor, may be used.

In some embodiments, the alkanoic acid, e.g., acetic acid, and the alkylenating agent, e.g., formaldehyde, are fed to the reactor at a molar ratio of at least 0.10:1, e.g., at least 0.75:1 or at least 1:1. In terms of ranges the molar ratio of alkanoic acid to alkylenating agent may range from 0.10:1 to 10:1 or from 0.75:1 to 5:1. In some embodiments, the reaction of the alkanoic acid and the alkylenating agent is conducted with a stoichiometric excess of alkanoic acid. In these instances, acrylate selectivity may be improved. As an example the acrylate selectivity may be at least 10% higher than a selectivity achieved when the reaction is conducted with an excess of alkylenating agent, e.g., at least 20% higher or at least 30% higher. In other embodiments, the reaction of the alkanoic acid and the alkylenating agent is conducted with a stoichiometric excess of alkylenating agent.

The condensation reaction may be conducted at a temperature of at least 250° C., e.g., at least 300° C., or at least 350° C. In terms of ranges, the reaction temperature may range from 200° C. to 500° C., e.g., from 250° C. to 400° C., or from 250° C. to 350° C. Residence time in the reactor may range from 1 second to 200 seconds, e.g., from 1 second to 100 seconds. Reaction pressure is not particularly limited, and the reaction is typically performed near atmospheric pressure. In one embodiment, the reaction may be conducted at a pressure ranging from 0 kPa to 4100 kPa, e.g., from 3 kPa to 345 kPa, or from 6 to 103 kPa.

Water may be present in amounts up to 60 wt. %, by weight of the reaction mixture, e.g., up to 50 wt. % or up to 40 wt. %. Water, however, is preferably reduced due to its negative effect on process rates and separation costs.

In one embodiment, an inert or reactive gas is supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors.

In one embodiment, the unreacted components such as the carboxylic acid and formaldehyde as well as the inert or reactive gases that remain are recycled to the reactor after sufficient separation from the desired product.

When the desired product is an unsaturated ester made by reacting an ester of an alkanoic acid ester with formaldehyde, the alcohol corresponding to the ester may also be fed to the reactor either with or separately to the other components. For example, when methyl acrylate is desired, methanol may be fed to the reactor. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity.

EXAMPLES

Catalyst Preparation

Catalyst 1

2.0 grams 40% colloidal silica was mixed with 50 ml deionized water and polyacrylic acid (1 mol equiv. of mol Ti). 10.98 grams Ti(OiPr)$_4$ was slowly added to 10 ml of 2-propanol. The diluted Ti(OiPr)$_4$ solution was slowly added to the colloidal silica mixture. This suspension was stirred for one hour at room temperature. 11.69 grams phosphoric acid was slowly added to form a suspension of hydrous titanium pyrophosphate. The suspension was stirred for one hour at room temperature. Separately, oxalic acid dehydrate was added to a solution of 12 ml ethylene glycol, 5 ml water, and polyacrylic acid (1 mol equiv per mol V). The oxalic acid mixture was heated to 85° C.; when the solution reached approximately 50° C., 2.26 grams solid ammonium metavanadate was slowly added with constant stirring. The oxalic acid/ammonium metavanadate mixture was stirred at 85° C. for one hour. The hot solution was added to the suspension of hydrous titanium pyrophosphate and rinsed with 5 ml of deionized water. The solution was stirred at room temperature for 30 minutes. The resultant material was dried with rotary evaporator set at 95° C. The tacky solid was further dried at 120° C. overnight to a solid consistency. The solid was calcined using the following profile:
i) drying with flowing air at 160° C. for 2 hours;
ii) drying with flowing air at 350° C. for 4 hours; iii) drying under static air at 450° C. for eight hours.

Comparative Catalysts A and B

The procedure for Catalyst A was repeated with the exception that no dispersing agent was used in the formation of the vanadium precursor.

2.0 grams 40% colloidal silica was mixed with 50 ml deionized water and 11.69 grams phosphoric acid. 10.98 grams Ti(OiPr)$_4$ was slowly added to 10 ml of 2-propanol. The diluted Ti(OiPr)$_4$ solution was slowly added to the colloidal silica mixture to form a suspension of hydrous titanium pyrophosphate. This suspension was stirred for one hour at room temperature. The suspension was stirred for one hour at room temperature. Separately, oxalic acid dehydrate was added to a solution of 12 ml ethylene glycol and 5 ml water. The oxalic acid mixture was heated to 85° C.; when the solution reached approximately 50° C., 2.26 grams solid ammonium metavanadate was slowly added with constant stirring. The oxalic acid/ammonium metavanadate mixture was stirred at 85° C. for one hour. The hot solution was added to the suspension of hydrous titanium pyrophosphate and rinsed with 5 ml of deionized water. The solution was stirred at room temperature for 30 minutes. The resultant material was dried with rotary evaporator set at 95° C. and calcined using the procedure for Catalyst 1.

The procedure for Catalyst B was repeated with the exception that no ethylene glycol or polyacrylic acid was used in the formation of the catalyst.

Example 1

The surface area and pore size of the catalysts of the invention and of the comparative examples were measured. The results are shown in Table 3.

TABLE 3

| Catalyst Sample | Dispersing Agent Mixture | Surface area (m$^2$/g) | Average Pore Size (nm) |
|---|---|---|---|
| 1 | Oxalic acid + ethylene glycol + polyacrylic acid (PAA) | 38.0 | 8.8 |
| A | Oxalic acid + ethylene glycol | 22.6* | 17.4* |
| B | Oxalic acid | 0.6 | 11.9 |

*Data point is an average of two experimental results.

As shown in Table 3, the use of oxalic acid alone resulted in a catalyst composition having a surface area of 0.6 m$^2$/g and an average pore size of 11.9 nm. In comparison, the use of oxalic acid with ethylene glycol yielded a catalyst composition having a surface area of 22.6 m$^2$/g and an average pore size from 17.4 nm. Thus, the addition of ethylene glycol led to an increase in surface area and an increase in average pore size. The use of polyacrylic acid (PAA) with ethylene glycol and oxalic acid yielded a catalyst composition having a surface area of 38.0 m$^2$/g and average pore size of 8.8 nm. Thus, the addition of the PAA, surprisingly and unexpectedly, led to an increase in surface area and a decrease in average pore size.

As shown below, the catalyst compositions of the invention with increased surface area and decreases average pore size, beneficially, provide for increased acetic acid conversions, while maintaining selectivity to the desired acrylates. As a result, acrylate space time yield is increased over comparable catalysts having the same components in the active phase, but different surface areas and average pore sizes.

Example 2

A reaction feed comprising acetic acid (9.1%), formaldehyde (17.3%), methanol (6.7%), water (38%), oxygen (4.06%), and nitrogen (24.8%) was passed through a fixed bed reactor comprising the Catalyst 1 and Comparative Catalyst A. The reaction was conducted at three temperatures, 340° C., 355° C., and 370° C. Acrylic acid and methyl acrylate (collectively, "acrylates") were produced. The conversions, selectivities, and space time yields are shown in Table 4.

TABLE 4

Acrylate Production

| Reaction Temperature | Catalyst Sample | Acetic Acid Conversion | Acrylate Selectivity | Acrylate Space Time Yield, g/liter of catalyst/hr |
|---|---|---|---|---|
| 340° C. | 1-1 | 27.1 | 68.9 | 74.3 |
| 340° C. | 1-2 | 30.3 | 68.1 | 67.1 |
| 340° C. | 1-3 | 24.1 | 71.1 | 71.3 |
| Avg. | | 27.2 | 69.4 | 70.9 |
| 340° C. | A-1 | 10.7 | 60.1 | 26.3 |
| 340° C. | A-2 | 10.9 | 59.7 | 28.1 |
| 340° C. | A-3 | 10.0 | 60.3 | 27.9 |
| Avg. | | 10.5 | 60.0 | 27.4 |
| 355° C. | 1-4 | 40.0 | 71.2 | 108.1 |
| 355° C. | 1-5 | 38.3 | 68.9 | 107.3 |
| 355° C. | 1-6 | 38.9 | 68.9 | 104.2 |

TABLE 4-continued

Acrylate Production

| Reaction Temperature | Catalyst Sample | Acetic Acid Conversion | Acrylate Selectivity | Acrylate Space Time Yield, g/liter of catalyst/hr |
|---|---|---|---|---|
| Avg. 355° C. | | 39.1 | 69.7 | 106.5 |
| 355° C. | A-4 | 27.7 | 62.0 | 43.6 |
| 355° C. | A-5 | 18.5 | 65.0 | 52.2 |
| 355° C. | A-6 | 19.9 | 64.5 | 50.5 |
| 355° C. | A-7 | 22.8 | 64.1 | 52.2 |
| 355° C. | A-8 | 19.7 | 63.6 | 56.7 |
| Avg. 370° C. | | 21.7 | 63.8 | 51.0 |
| 370° C. | 1-7 | 51.2 | 72.0 | 148.3 |
| 370° C. | 1-8 | 52.4 | 70.3 | 141.9 |
| 370° C. | 1-9 | 52.6 | 70.3 | 141.0 |
| Avg. 370° C. | | 52.1 | 70.9 | 143.7 |
| 370° C. | A-9 | 35.7 | 68.9 | 87.7 |
| 370° C. | A-10 | 35.4 | 68.3 | 88.9 |
| 370° C. | A-11 | 34.4 | 69.2 | 89.9 |
| 370° C. | A-12 | 37.8 | 67.7 | 91.7 |
| 370° C. | A-13 | 37.4 | 66.6 | 86.4 |
| 370° C. | A-14 | 35.4 | 69.3 | 96.0 |
| Avg. | | 36.0 | 68.3 | 90.1 |

As shown in Table 4, the use of dispersing agent in preparing the catalyst composition surprisingly and unexpectedly provides for significant improvements in acetic acid conversion and improved selectivity to acrylates. These improvements result in higher productivities, e.g., space time yields in all three temperatures.

Also, as shown in Table 4, the inventive catalyst composition not only maintains selectivities to acrylates, but in some cases provide for slight increases in acrylate selectivity.

In addition, as shown in Table 5, the inventive catalyst compositions also beneficially provide for decreases in the selectivities to carbon monoxide and a slight increase to methyl methacrylate.

TABLE 5

Acrylate Production

| Reaction Temperature | Catalyst Sample | Acetic Acid Conversion | Carbon Monoxide Selectivity | Methyl Acrylate Selectivity |
|---|---|---|---|---|
| 340° C. | 1-1 | 27.1 | 17.7 | 20.0 |
| 340° C. | 1-2 | 30.3 | 17.0 | 23.0 |
| 340° C. | 1-3 | 24.1 | 15.4 | 20.6 |
| Avg. 340° C. | | 27.2 | 16.7 | 21.2 |
| 340° C. | A-1 | 10.7 | 25.7 | 17.9 |
| 340° C. | A-2 | 10.9 | 25.4 | 17.7 |
| 340° C. | A-3 | 10.0 | 24.9 | 18.2 |
| Avg. 355° C. | | 10.5 | 25.3 | 17.9 |
| 355° C. | 1-4 | 40.0 | 15.4 | 17.9 |
| 355° C. | 1-5 | 38.3 | 17.6 | 17.3 |
| 355° C. | 1-6 | 38.9 | 18.0 | 17.2 |
| Avg. 355° C. | | 39.1 | 17.0 | 17.5 |
| 355° C. | A-4 | 27.7 | 25.8 | 13.0 |
| 355° C. | A-5 | 18.5 | 22.9 | 17.1 |
| 355° C. | A-6 | 19.9 | 23.0 | 16.2 |
| 355° C. | A-7 | 22.8 | 23.8 | 16.1 |
| 355° C. | A-8 | 19.7 | 24.2 | 16.2 |
| Avg. 370° C. | | 21.7 | 23.9 | 15.7 |
| 370° C. | 1-7 | 51.2 | 14.5 | 15.0 |
| 370° C. | 1-8 | 52.4 | 15.8 | 14.5 |
| 370° C. | 1-9 | 52.6 | 15.8 | 14.4 |
| Avg. 370° C. | | 52.1 | 15.4 | 14.6 |
| 370° C. | A-9 | 35.7 | 19.9 | 14.0 |
| 370° C. | A-10 | 35.4 | 19.8 | 15.6 |
| 370° C. | A-11 | 34.4 | 19.3 | 14.8 |
| 370° C. | A-12 | 37.8 | 21.1 | 13.9 |
| 370° C. | A-13 | 37.4 | 22.3 | 14.1 |
| 370° C. | A-14 | 35.4 | 18.9 | 15.2 |
| Avg. | | 36.0 | 20.2 | 14.6 |

As shown in Table 5, low carbon monoxide selectivities were shown at 340° C., 355° C. and 370° C. Although methyl acrylate selectivity increased slightly, the overall product selectivity for acrylate increased significantly. Thus, the use of dispersing agents in the preparation of the catalyst composition is beneficial to the overall production of acrylate.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A catalyst composition, comprising:
   vanadium;
   titanium; and
   the catalyst composition having a surface area of at least 22.6 m²/g and a plurality of pores, the plurality of pores having an average pore diameter less than 11.9 nm.

2. The catalyst composition of claim 1, further comprising a dispersing agent selected from the group consisting of polyacrylic acid, polyvinyl alcohol, an ionic surfactant, polysiloxane and clay.

3. The catalyst composition of claim 2, wherein the molar ratio of the dispersing agent to the combination of vanadium and titanium in an active phase of the catalyst ranges from 0.1:10 to 10:1.

4. The catalyst composition of claim 2, wherein the molar ratio of the dispersing agent to vanadium in an active phase of the catalyst composition ranges from 0.1:1.0 to 10:1.

5. The catalyst composition of claim 2, wherein the molar ratio of the dispersing agent to titanium in an active phase of the catalyst composition ranges from 0.0:1.0 to 10:1.

6. The catalyst composition of claim 1, wherein the molar ratio of vanadium to titanium in an active phase of the catalyst composition is greater than 0.5:1.

7. The catalyst composition of claim 1, wherein an active phase of the catalyst composition comprises from 5 wt. % to 40 wt. % titanium.

8. The catalyst composition of claim 1, wherein an active phase of the catalyst composition comprises from 1 wt. % to 40 wt. % vanadium.

9. The catalyst composition of claim 1, wherein the catalyst further comprises:
from 15 wt. % to 45 wt. % phosphorus; and
from 30 wt. % to 75 wt. % oxygen.

10. The composition of claim 1, wherein the catalyst further comprises a support.

11. The composition of claim 10, wherein the support is selected from the group consisting of silica, alumina, zirconia, titania, aluminosilicates, zeolitic materials, and mixtures thereof.

12. A catalyst composition, comprising:
vanadium;
titanium; and
a dispersing agent selected from the group consisting of an organic polymer, an ionic surfactant, a polysiloxane and a clay.

13. The catalyst composition of claim 12, comprises at least from 0.01 wt. % to 10 wt. % of the dispersing agent.

14. A process for producing a catalyst composition, comprising:
(a) contacting a titanium precursor, a vanadium precursor, phosphoric acid, a reducing agent, and a dispersing agent selected from the group consisting of an organic polymer, a polysiloxane, an ionic surfactant and a clay, to form a catalyst precursor mixture; and
(b) drying and calcining the catalyst precursor mixture to form the catalyst composition comprising titanium and vanadium and having a surface area of at least 22.6 m$^2$/g and a plurality of pores, wherein the plurality of pores having an average pore diameter less than 11.9 nm.

15. The process of claim 14, wherein step (a) comprises:
contacting the titanium precursor, phosphoric acid, and the dispersing agent to form a titanium precursor mixture;
contacting the vanadium precursor with a mixture of a reducing agent and the dispersing agent, to form a vanadium mixture; and
contacting the titanium precursor mixture with the vanadium precursor mixture to form the catalyst precursor mixture.

16. The process of claim 15, further comprising heating the titanium precursor mixture to a temperature ranging from 20° C. to 100° C. before contacting the vanadium precursor mixture with the titanium precursor mixture.

17. The process of claim 15, further comprising heating the vanadium precursor mixture to a temperature ranging from 50° C. to 100° C. for one hour.

18. The process of claim 14, wherein the organic polymer is selected from the group consisting of polyacrylic acid and polyvinyl alcohol.

19. The process of claim 14, wherein the titanium precursor is selected from a group consisting of Ti(OR)$_4$, L$_x$Ti(OR)$_y$, complexes, TiCl$_z$, hydrated titania sols and colloidal TiO$_2$, wherein
R=methyl, ethyl, propyl, isopropyl, and butyl;
L=bidentate ligands;
x=1-3;
y=1-3; and
z=3-4.

20. The process of claim 14, wherein the dispersing agent is polyacrylic acid.

21. The process of claim 14, wherein the vanadium precursor comprises ammonium metavanadate.

22. The process of claim 14, wherein step (b) comprises calcining the catalyst composition.

23. The process of claim 22, wherein the calcining comprises:
contacting the catalyst composition with flowing air at a first temperature;
contacting the catalyst composition with flowing air at a second temperature greater than the first temperature; and
contacting the catalyst composition with static air at a third temperature greater than the first and second temperature.

24. The process of claim 23, wherein the first temperature ranges from 110° C. to 210° C., the second temperature ranges from 300° C. to 400° C. and the third temperature ranges from 400° C. to 500° C.

25. A catalyst composition produced by the process of claim 14.

26. A process for producing a catalyst composition, comprising:
(a) contacting a titanium precursor, phosphoric acid, and a dispersing agent selected from a group consisting of an organic polymer, a polysiloxane, an ionic surfactant and a clay;
(b) contacting a vanadium precursor with a mixture of a reducing agent and the dispersing agent, to form a vanadium mixture;
(c) contacting the titanium pyrophosphate mixture with the vanadium mixture to form the catalyst composition having a surface area of at least 22.6 m$^2$/g and a plurality of pores, wherein the plurality of pores having an average pore diameter less than 11.9 nm; and
(d) removing at least a portion of the dispersing agent by calcining the catalyst composition.

27. A process for producing acrylic acid comprising the steps of:
contacting acetic acid and an alkylenating agent over a catalyst composition to produce acrylic acid and/or acrylate,
wherein the catalyst composition comprises vanadium and titanium,
wherein the catalyst composition has a surface area of at least 22.6 m$^2$/g, and
wherein the catalyst composition comprises a plurality of pores, the plurality of pores having an average pore diameter less than 11.9 nm.

28. The process of claim 27, wherein the catalyst composition further comprises a dispersing agent selected from the group consisting of an organic polymer, an ionic surfactant, polysiloxane and clay, wherein the dispersing agent has a functional group.

29. The process of claim 28, wherein the molar ratio of the functional group of the dispersing agent to the combination of vanadium and titanium catalyst in the active phase ranges from 0.1:10 to 10:0.1.

30. The process of claim 28, wherein the organic polymer is selected from the group consisting of polyacrylic acid, polyvinyl alcohol, poly(methyl methacrylate), poly(ethylene oxide), poly(ethylene glycol), polyethylenimine, copolymers, ionic surfactants, and polysiloxanes.

31. The process of claim 28, wherein the dispersing agent is a metal salt of an ionic surfactant.

32. The process of claim 28, wherein the alkylenating agent comprises formaldehyde.

33. The process of claim 27, wherein the overall acetic acid conversion is at least 11% at 340° C.

34. The process of claim 27, wherein the over acetic acid conversion is at least 28% at 355° C.

35. The process of claim 27, wherein the over acetic acid conversion is at least 38% at 370° C.

36. The process of claim 27, wherein the space time yield of the combination of acrylic acid and acrylate is at least 28 grams/liter of catalyst/hour at 340° C.

37. The process of claim 27, wherein the space time yield of the combination of acrylic acid and acrylate is at least 53 grams/liter of catalyst/hour at 355° C.

38. The process of claim 27, wherein the space time yield of the combination of acrylic acid and acrylate is at least 97 grams/liter of catalyst/hour at 370° C.

39. A process for producing acrylic acid comprising the steps of:
   contacting acetic acid and an alkylenating agent over a catalyst composition to produce acrylic acid and/or acrylate,
   wherein the catalyst composition comprises vanadium, titanium, and a dispersing agent selected from the group consisting of an organic polymer, an ionic surfactant, a polysiloxane and a clay.

* * * * *